(12) United States Patent
Kim et al.

(10) Patent No.: US 9,211,156 B2
(45) Date of Patent: Dec. 15, 2015

(54) MAP AND ABLATE CLOSED-LOOP COOLED ABLATION CATHETER WITH FLAT TIP

(71) Applicant: Boston Scientific Scimed, Inc., Maple Grove, MN (US)

(72) Inventors: Isaac J. Kim, San Jose, CA (US); Zaya Tun, Livermore, CA (US); Josef V. Koblish, Sunnyvale, CA (US); Minhchau N. Cao, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 162 days.

(21) Appl. No.: 14/029,562

(22) Filed: Sep. 17, 2013

(65) Prior Publication Data

US 2014/0081112 A1    Mar. 20, 2014

Related U.S. Application Data

(60) Provisional application No. 61/702,616, filed on Sep. 18, 2012.

(51) Int. Cl.
*A61B 5/042* (2006.01)
*A61B 18/14* (2006.01)
(Continued)

(52) U.S. Cl.
CPC ......... *A61B 18/1492* (2013.01); *A61B 5/04012* (2013.01); *A61B 5/0422* (2013.01); *A61B 5/4836* (2013.01); *A61B 18/1206* (2013.01); *A61B 18/18* (2013.01); *A61B 2018/00005* (2013.01); *A61B 2018/00023* (2013.01); *A61B 2018/00029* (2013.01); *A61B 2018/00839* (2013.01)

(58) Field of Classification Search
CPC ........................ A61B 5/0422; A61B 18/1492
USPC ............................................ 600/374; 606/41
See application file for complete search history.

(56) References Cited

U.S. PATENT DOCUMENTS

| | | |
|---|---|---|
| 4,732,149 A | 3/1988 | Sutter |
| 4,763,660 A | 8/1988 | Kroll et al. |

(Continued)

FOREIGN PATENT DOCUMENTS

| | | |
|---|---|---|
| EP | 1343426 B1 | 9/2003 |
| EP | 1343427 B1 | 9/2003 |

(Continued)

OTHER PUBLICATIONS

International Search Report and Written Opinion issued in PCT/US2013/060194, mailed Jan. 29, 2014, 10 pages.

(Continued)

*Primary Examiner* — Lee S Cohen
(74) *Attorney, Agent, or Firm* — Faegre Baker Daniels LLP

(57) ABSTRACT

A system for performing mapping and ablation functions includes a catheter sized and shaped for vascular access. The catheter includes an elongate body extending between a proximal end and a distal end and having at least one inner fluid lumen. The catheter further includes a tip section positioned proximate to the distal end of the body. The tip section includes a proximal portion and a distal portion. The distal portion can have a distal end that can be substantially planar. The system also includes one or more electrode structures exposed at the tip section such that the one or more electrode structures disposed proximate the substantially planar distal end of the tip section.

16 Claims, 5 Drawing Sheets

(51) Int. Cl.
*A61B 5/00* (2006.01)
*A61B 18/18* (2006.01)
*A61B 18/12* (2006.01)
*A61B 5/04* (2006.01)
*A61B 18/00* (2006.01)

(56) References Cited

U.S. PATENT DOCUMENTS

| | | |
|---|---|---|
| 5,217,460 A | 6/1993 | Knoepfler |
| 5,254,088 A | 10/1993 | Lundquist et al. |
| 5,318,589 A | 6/1994 | Lichtman |
| 5,331,966 A | 7/1994 | Bennett et al. |
| 5,383,874 A | 1/1995 | Jackson et al. |
| 5,385,146 A | 1/1995 | Goldreyer |
| 5,391,199 A | 2/1995 | Ben-Haim |
| 5,398,683 A | 3/1995 | Edwards et al. |
| 5,462,521 A | 10/1995 | Brucker et al. |
| 5,482,054 A | 1/1996 | Slater et al. |
| 5,500,012 A | 3/1996 | Brucker et al. |
| 5,573,535 A | 11/1996 | Viklund |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,800,482 A | 9/1998 | Pomeranz et al. |
| 5,830,213 A | 11/1998 | Panescu et al. |
| 5,868,735 A | 2/1999 | Lafontaine |
| 5,871,483 A | 2/1999 | Jackson et al. |
| 5,916,213 A | 6/1999 | Haissaguerre et al. |
| 6,027,500 A | 2/2000 | Buckles et al. |
| 6,050,994 A | 4/2000 | Sherman |
| 6,059,778 A | 5/2000 | Sherman |
| 6,064,905 A | 5/2000 | Webster, Jr. et al. |
| 6,070,094 A | 5/2000 | Swanson et al. |
| 6,099,524 A * | 8/2000 | Lipson et al. .................. 606/41 |
| 6,116,027 A | 9/2000 | Smith et al. |
| 6,171,305 B1 | 1/2001 | Sherman |
| 6,200,314 B1 | 3/2001 | Sherman |
| 6,233,491 B1 | 5/2001 | Kordis et al. |
| 6,290,697 B1 | 9/2001 | Tu et al. |
| 6,475,213 B1 | 11/2002 | Whayne et al. |
| 6,488,678 B2 | 12/2002 | Sherman |
| 6,491,710 B2 | 12/2002 | Satake |
| 6,517,533 B1 | 2/2003 | Swaminathan |
| 6,517,534 B1 | 2/2003 | McGovern et al. |
| 6,537,271 B1 | 3/2003 | Murray et al. |
| 6,547,788 B1 | 4/2003 | Maguire et al. |
| 6,575,966 B2 | 6/2003 | Lane et al. |
| 6,579,278 B1 | 6/2003 | Bencini |
| 6,602,242 B1 | 8/2003 | Fung et al. |
| 6,640,120 B1 | 10/2003 | Swanson et al. |
| 6,656,174 B1 | 12/2003 | Hegde et al. |
| 6,666,862 B2 | 12/2003 | Jain et al. |
| 6,735,465 B2 | 5/2004 | Panescu |
| 6,796,979 B2 | 9/2004 | Lentz |
| 6,796,980 B2 | 9/2004 | Hall |
| 6,811,550 B2 | 11/2004 | Holland et al. |
| 6,837,884 B2 | 1/2005 | Woloszko |
| 6,917,834 B2 | 7/2005 | Koblish et al. |
| 6,922,579 B2 | 7/2005 | Taimisto et al. |
| 6,932,811 B2 | 8/2005 | Hooven et al. |
| 6,950,689 B1 | 9/2005 | Willis et al. |
| 6,952,615 B2 | 10/2005 | Satake |
| 7,047,068 B2 | 5/2006 | Haissaguerre |
| 7,097,643 B2 | 8/2006 | Cornelius et al. |
| 7,112,198 B2 | 9/2006 | Satake |
| 7,247,155 B2 | 7/2007 | Hoey et al. |
| 7,347,857 B2 | 3/2008 | Anderson et al. |
| 7,438,714 B2 | 10/2008 | Phan |
| 7,569,052 B2 | 8/2009 | Phan et al. |
| 7,736,362 B2 | 6/2010 | Eberl et al. |
| 7,740,629 B2 | 6/2010 | Anderson et al. |
| 7,799,025 B2 | 9/2010 | Wellman |
| 7,819,863 B2 | 10/2010 | Eggers et al. |
| 8,579,889 B2 | 11/2013 | Bencini |
| 8,740,900 B2 * | 6/2014 | Kim et al. ................... 606/46 |
| 2002/0087208 A1 | 7/2002 | Koblish et al. |
| 2003/0088240 A1 | 5/2003 | Saadat |
| 2004/0092806 A1 | 5/2004 | Sagon et al. |
| 2004/0116793 A1 | 6/2004 | Taimisto et al. |
| 2004/0215186 A1 | 10/2004 | Cornelius et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2006/0089634 A1 | 4/2006 | Anderson et al. |
| 2006/0161146 A1 | 7/2006 | Cornelius et al. |
| 2006/0247607 A1 | 11/2006 | Cornelius et al. |
| 2006/0253116 A1 | 11/2006 | Avitall et al. |
| 2007/0049925 A1 | 3/2007 | Phan et al. |
| 2007/0270794 A1 | 11/2007 | Anderson et al. |
| 2008/0058836 A1 | 3/2008 | Moll et al. |
| 2008/0140065 A1 | 6/2008 | Rioux et al. |
| 2008/0161795 A1 | 7/2008 | Wang et al. |
| 2008/0195089 A1 | 8/2008 | Thiagalingam et al. |
| 2008/0243214 A1 | 10/2008 | Koblish |
| 2008/0281322 A1 | 11/2008 | Sherman et al. |
| 2009/0048591 A1 | 2/2009 | Ibrahim et al. |
| 2009/0062790 A1 | 3/2009 | Malchano et al. |
| 2009/0062795 A1 | 3/2009 | Vakharia et al. |
| 2009/0093811 A1 | 4/2009 | Koblish et al. |
| 2009/0131932 A1 | 5/2009 | Vakharia et al. |
| 2009/0182316 A1 | 7/2009 | Bencini |
| 2009/0240247 A1 | 9/2009 | Rioux et al. |
| 2009/0259274 A1 | 10/2009 | Simon et al. |
| 2009/0287202 A1 | 11/2009 | Ingle et al. |
| 2010/0010487 A1 | 1/2010 | Phan et al. |
| 2010/0106155 A1 | 4/2010 | Anderson et al. |
| 2010/0152728 A1 | 6/2010 | Park et al. |
| 2010/0168557 A1 | 7/2010 | Deno et al. |
| 2010/0331658 A1 | 12/2010 | Kim et al. |
| 2011/0028820 A1 | 2/2011 | Lau et al. |
| 2011/0112569 A1 | 5/2011 | Friedman et al. |
| 2011/0125143 A1 | 5/2011 | Gross et al. |
| 2012/0330304 A1 | 12/2012 | Vegesna et al. |
| 2014/0058375 A1 | 2/2014 | Koblish |
| 2014/0073893 A1 | 3/2014 | Bencini |
| 2014/0081111 A1 | 3/2014 | Tun et al. |
| 2014/0107453 A1 | 4/2014 | Maskara et al. |
| 2014/0107636 A1 | 4/2014 | Bencini |

FOREIGN PATENT DOCUMENTS

| | | |
|---|---|---|
| EP | 1502542 A1 | 2/2005 |
| EP | 1547537 A1 | 6/2005 |
| EP | 0985423 B1 | 4/2006 |
| WO | WO9221278 A1 | 12/1992 |
| WO | WO9725916 A1 | 7/1997 |
| WO | WO9725917 A1 | 7/1997 |
| WO | WO9736541 A1 | 10/1997 |
| WO | WO9858681 A2 | 12/1998 |
| WO | WO9927862 A1 | 6/1999 |
| WO | WO0029062 A2 | 5/2000 |
| WO | WO0158372 A1 | 8/2001 |
| WO | WO0164145 A1 | 9/2001 |
| WO | WO0205868 A2 | 1/2002 |
| WO | WO0209599 A2 | 2/2002 |
| WO | WO0219934 A1 | 3/2002 |
| WO | WO0247569 A1 | 6/2002 |
| WO | WO02102234 A2 | 12/2002 |
| WO | WO03039338 A2 | 5/2003 |
| WO | WO2007079278 A1 | 7/2007 |
| WO | WO2008118992 A1 | 10/2008 |
| WO | WO2010056771 A1 | 5/2010 |

OTHER PUBLICATIONS

International Search Report and Written Opinion issued in PCT/US2013/056211, mailed Jan. 20, 2014.

International Search Report and Written Opinion issued in PCT/US2013/060183, mailed Jan. 27, 2014, 10 pages.

(56) References Cited

OTHER PUBLICATIONS

International Search Report and Written Opinion issued in PCT/US2013/060194, mailed Jan. 29, 2014.

Goldberg, S. Nahum et al., "Variables Affecting Proper System Grounding for Radiofrequency Ablation in an Animal Model", JVIR, vol. 11, No. 8, Sep. 2000, pp. 1069-1075.

International Search Report and Written Opinion issued in PCT/US2008/058324, dated Aug. 18, 2008, 11 pages.

International Search Report and Written Opinion issued in PCT/US2012/055309, mailed Nov. 19, 2012, 13 pages.

Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.

Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.

Partial International Search Report issued in PCT/US2012/0551545, mailed Dec. 20, 2012, 7 pages.

Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.

* cited by examiner

MAP AND ABLATE CLOSED-LOOP COOLED ABLATION CATHETER WITH FLAT TIP

CROSS-REFERENCE TO RELATED APPLICATION

This application claims the benefit of Provisional Application No. 61/702,616, filed Sep. 18, 2012, which is incorporated herein by reference in its entirety.

TECHNICAL FIELD

The present disclosure generally relates to therapies for treating cardiac conditions. More particularly, the present disclosure relates to a system for mapping and ablating target tissue of a patient.

BACKGROUND

Atrial fibrillation is a condition in the heart causing irregular heartbeats due to generation of abnormal electrical signals. Various treatment regimens may be followed for treating arrhythmias, such as anti-arrhythmic medications and catheter ablation.

Catheter ablation is a minimally invasive procedure that involves killing an abnormal muscle responsible for tissue dysfunction. This produces a small area of dead heart muscle called a lesion. In order to make lesions and thereby treat arrhythmia, abnormal heart muscles are first targeted and mapped, such as through a mapping technique. A catheter used for such purposes generally includes one or more mapping electrodes configured to carry out mapping functions and an ablation electrode configured to carry out the ablation function. Mapping typically involves percutaneously introducing the catheter having one or more mapping electrodes into the patient, passing the catheter through a blood vessel (e.g., the femoral vein or artery) and into an endocardial site (e.g., an atrium or ventricle of the heart) to map bioelectrical signals arising from the myocardial tissues and thereby, recognizing the tissue that is the source of the arrhythmia. The tip of the ablation catheter including the tip ablation electrode can then deliver energy to the abnormal heart muscle, which disables it.

SUMMARY

Disclosed herein are embodiments of an ablation electrode including one or more mapping electrodes exposed at an exterior surface thereof proximate a substantially planar distal end of a map and ablate catheter.

In Example 1, a system for performing mapping and ablation functions includes a catheter sized and shaped for vascular access. The catheter includes an elongate body extending between a proximal end and a distal end and having at least one inner fluid lumen. The catheter further includes a tip section positioned proximate to the distal end of the body. The tip section includes a proximal portion and a distal portion. The distal portion has a distal end that is substantially planar. The system also includes one or more electrode structures exposed at the tip section such that the one or more electrode structures are disposed proximate to the substantially planar distal end of the tip section.

In Example 2, the system according to Example 1, wherein the catheter includes at least one inner fluid lumen, wherein the ablation electrode comprises an exterior wall that defines an open interior region within the ablation electrode, and wherein the system further comprises a thermal mass within the open interior region and a cooling chamber in fluid communication with the at least one inner fluid lumen and positioned proximally to the thermal mass.

In Example 3, the system according to either Example 1 or Example 2, wherein the thermal mass includes at least one fluid passageway therethrough.

In Example 4, the system according to any of Examples 1-3, wherein the at least one inner fluid lumen comprises a first inner fluid lumen extending along at least a portion of the elongate body. The first inner fluid lumen is configured for fluid communication with a fluid reservoir including a cooling fluid, and further configured to deliver the cooling fluid from the fluid reservoir to the cooling chamber. The inner fluid lumen further comprises a second inner fluid lumen extending along at least a portion of the elongate body. The second inner fluid lumen is configured for fluid communication with the fluid reservoir, and further configured to return the cooling fluid circulated within the cooling chamber to the fluid reservoir.

In Example 5, the system according to any of Examples 1-4, further comprising a temperature sensor positioned at least partially within the thermal mass and comprising a material of high thermal conductivity.

In Example 6, the system according to any of Examples 1-5, wherein the tip section comprises an ablation electrode configured to deliver radio frequency (RF) energy for an RF ablation procedure.

In Example 7, the system according to any of Examples 1-6, the one or more mapping electrode structures are formed on the ablation electrode.

In Example 8, the system according to any of Examples 1-7, wherein each of the one or more electrode structures comprise a mapping electrode and a noise artifact isolator comprising an electrical insulator disposed between the mapping electrode and the ablation electrode.

In Example 9, the system according to any of Examples 1-8, wherein the one or more mapping electrode structures are disposed within about 1.0 mm of the planar distal end of the tip section.

In Example 10, the system according to any of the Examples 1-9, further comprising one or more mapping ring electrodes disposed on the body proximal to the one or more electrode structures.

In Example 11, a system for performing mapping and ablation functions includes a radio frequency (RF) generator, a fluid reservoir and a pump, and a mapping signal processor. The system further includes a catheter sized and shaped for vascular access, including an elongate body extending between a proximal end and a distal end and having at least one inner fluid lumen. The system further includes an ablation electrode coupled to the distal end of the body, and operably connected to the RF generator. The ablation electrode includes an exterior wall that defines an open interior region within the ablation electrode, which includes a proximal portion and a distal portion. The distal portion has a distal end that is substantially planar. The system further comprises one or more mapping electrodes structures operably connected to the mapping signal processor, the one or more mapping electrode structures exposed at an exterior of the ablation electrode proximate to the substantially planar distal end.

In Example 12, the system according to Example 11, wherein each of the one or more electrode structures comprises a mapping electrode and a noise artifact isolator comprising an electrical insulator disposed between the mapping electrode and the ablation electrode.

In Example 13, the system according to either Example 11 or Example 12, further comprising a thermal mass within the open interior region and a cooling chamber in fluid communication with the at least one inner fluid lumen of the elongate body and positioned proximate to the thermal mass.

In Example 14, the system according to Example 13, wherein the thermal mass includes at least one fluid passageway therethrough.

In Example 15, the system according to any of the Examples 11-14, wherein the at least one inner fluid lumen comprises a first inner fluid lumen extending along at least a portion of the elongate body. The first inner fluid lumen in fluid communication with the fluid reservoir and pump such that the pump pushes cooling fluid from the fluid reservoir to the cooling chamber via the first inner fluid lumen. The inner fluid lumen further comprises a second inner fluid lumen extending along at least a portion of the elongate body. The second inner fluid lumen is in fluid communication with the fluid reservoir and pump such that the pump pulls the cooling fluid circulated within the cooling chamber to the fluid reservoir via the second inner fluid lumen.

In Example 16, a system for performing mapping and ablation functions includes a catheter sized and shaped for vascular access and including an elongate body extending between a proximal end and a distal end, and having at least one inner fluid lumen. The system further comprises an ablation electrode coupled to the distal end of the catheter body. The ablation electrode is configured to deliver radio frequency (RF) energy for an RF ablation procedure. The ablation electrode includes an exterior wall that defines an open interior region within the ablation electrode. The ablation electrode includes a proximal portion and a distal portion, wherein the distal portion has a distal end that is substantially planar. The system also comprises a thermal mass within the open interior region. The system further comprises a cooling chamber in fluid communication with the at least one inner fluid lumen of the elongate body and positioned proximally to the thermal mass and one or more mapping electrode structures exposed at an exterior of the ablation electrode.

In Example 17, the system according to Example 16, further comprising one or more mapping ring electrodes disposed on the body proximal to the one or more electrode structures.

In Example 18, the system according to Example 16 or Example 17, wherein each of the one or more electrode structures comprise a mapping electrode and a noise artifact isolator comprising an electrical insulator disposed between the mapping electrode and the ablation electrode.

In Example 19, the system according to any of Examples 16-18, wherein the at least one inner fluid lumen comprises a first inner fluid lumen extending along at least a portion of the elongate body. The first inner fluid lumen is configured for fluid communication with a fluid reservoir includes a cooling fluid. The first inner fluid is further configured to deliver the cooling fluid from the fluid reservoir to the cooling chamber. The at least one inner fluid lumen further comprises a second inner fluid lumen extending along at least a portion of the elongate body. The second inner fluid lumen is configured for fluid communication with the fluid reservoir; the second inner fluid lumen is further configured to return the cooling fluid circulated within the cooling chamber to the fluid reservoir.

In Example 20, the system according to the Examples 16-19, further comprising one or more mapping ring electrodes disposed on the body proximal to the one or more electrode structures, the one or more ring electrodes operably connected to the mapping signal processor.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
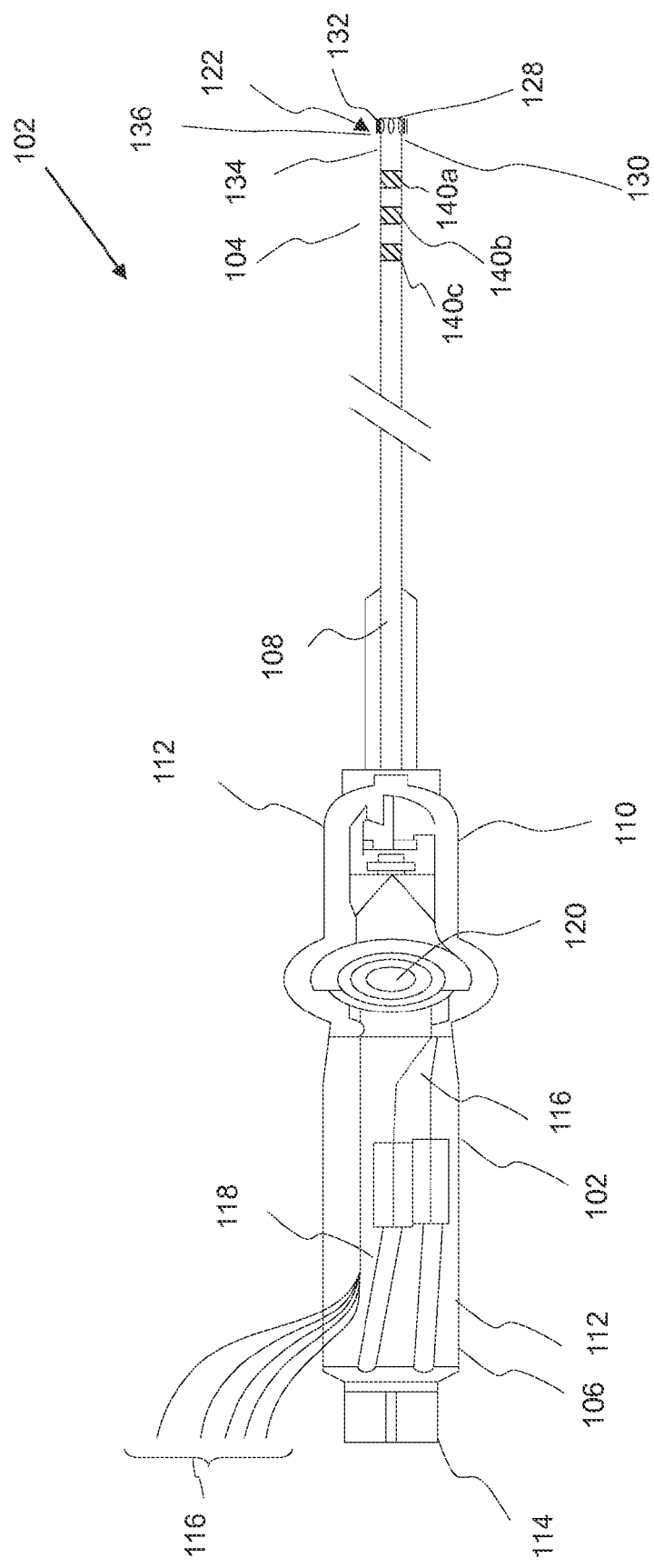
FIG. 1 is a schematic view of an embodiment of a system for performing mapping and ablation functions.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of an embodiment of a system 100 for performing mapping and ablation functions, according to some embodiments. The system 100 includes a catheter 102 sized and shaped for vascular access. The catheter 102 includes a distal end portion 104 and a proximal end portion 106. The catheter 102 defines at least one inner fluid lumen 108. The catheter includes an elongate body 110 and a handle 112.

The handle 112 includes a connection port 114 through which external energy sources can be operably coupled. The handle 112 includes a plurality of conduits, conductors, and wires to facilitate control of the catheter 102. The plurality of conduits, conductors, and wires are collectively referred to as a wire assembly 116. The elongate body 110 includes a control mechanism 118 and an articulating mechanism 120. The control mechanism 118 is placed at the handle 112 of the catheter 102. The articulating mechanism 120 is placed on the elongate body 110 such that the control mechanism 118 controls the articulating mechanism 120. The elongate body 110 also includes a tip section 122 at the distal end portion 104. The elongate body 110 houses the wire assembly 116 for transmitting sensed signals and/or ablation energy between the distal end portion 104 and proximal end portion 106.

The handle 112 is configured to be comfortably held by a practitioner during a treatment procedure involving ablation. The handle 112 may be comprised of a durable and rigid material, such as medical grade plastic, and ergonomically molded to allow the practitioner to easily manipulate the catheter 102. The elongate body 110 can be preferably about 1.67 mm to 3 mm in diameter, and between 800 mm and 1500 mm in length. The elongate body 110 can have a circular cross-sectional geometry. However, other cross-sectional shapes, such as elliptical, rectangular, triangular, and various other shapes, can be provided. In some embodiments, the elongate body 110 can be preformed of an inert, resilient plastic material that retains its shape and does not soften significantly at body temperature; for example, Pebax(R), polyethylene, or Hytrel(R) (polyester). In some embodiments, the elongate body 110 can be made of a variety of materials, including, but not limited to, metals and polymers. The elongate body 110 can be flexible so that it is capable of winding through a tortuous path that leads to a target site. In some embodiments, the elongate body 110 can be semi-rigid, i.e., by being made of a stiff material, or by being reinforced with a coating or coil, to limit the amount of flexing. The articulating mechanism 120 of the elongate body 110 facilitates insertion of the catheter 102 through a body lumen (e.g., vasculature) and/or placement of electrodes at a target tissue location. The articulating mechanism 120 provides one or more degrees of freedom and permits up/down and/or left/right articulation. In some embodiments, the movement of the distal end portion 104 of the catheter 102 (such as to wind through the tortuous path that leads to a target site) can be controlled by the control mechanism 118. In some embodiments, the distal end portion 104 of the catheter 102 can be deflected or bent at the articulating mechanism 120.

The tip section 122 includes a distal end 128 that is substantially planar or substantially orthogonal to the tip section 122 and/or distal end portion 104. The tip section 122 includes an ablation electrode 130 configured to deliver radio frequency (RF) energy for an RF ablation procedure. The ablation electrode 130 is formed from a conductive material. For example, in some embodiments the ablation electrode 130 is comprised of a platinum-iridium alloy (e.g., 90% platinum and 10% iridium). The tip section 122 also includes one or more mapping electrode structures 132 exposed at an exterior surface 134 of the ablation electrode 130. Each of the one or more mapping electrode structures 132 includes a mapping electrode 136. In some embodiments, the one or more mapping electrode structures 132 are disposed proximate to the substantially planar distal end 128 of the tip section 122. In some embodiments, the one or more mapping electrode structures 132 are disposed approximately 1.0 mm from the planar distal end 128 of the tip section 122, but the one or more mapping electrode structures 132 may alternatively be deposited other distances from the planar distal end 128. In some embodiments, the one or more mapping electrode structures 132 are deposited on the ablation electrode 130.

The system 100 may also include one or more mapping ring electrodes 140. The mapping ring electrodes 140 can be configured to map the bioelectrical signals arising from the myocardial tissues and thereby recognize the tissues that are the source of arrhythmia. The mapping ring electrodes 140 can include a distal mapping ring electrode 140a, a medial mapping ring electrode 140b, and a proximal mapping ring electrode 140c. The mapping ring electrodes 140a, 140b, and 140c as well as the ablation electrode 126 are capable of forming a bipolar mapping electrode pair. In particular, the ablation electrode 126 and distal mapping ring electrode 140a together can form a first bipolar mapping electrode pair, the distal mapping ring electrode 140a and the medial mapping ring electrode 140b together can form a second bipolar mapping electrode pair, the medial mapping ring electrode 140b and the proximal mapping ring electrode 140c together can form a third bipolar mapping electrode pair, and any combination thereof. Like the mapping electrodes structures 132, the mapping ring electrodes 140a-140c are also operably coupled to the mapping signal processor to map electrical events in the myocardial tissues.

Figure 2:
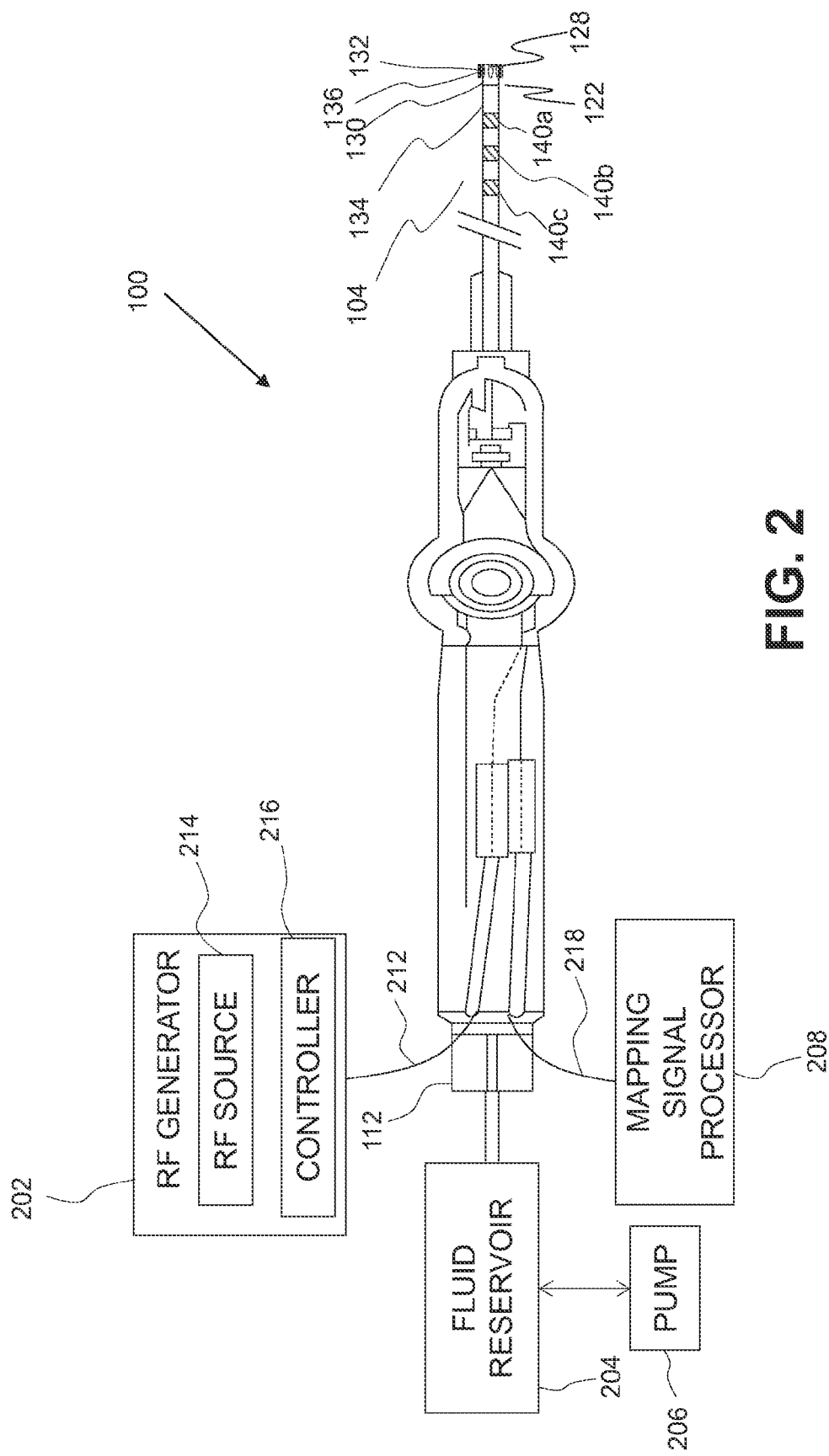
FIG. 2 illustrates an embodiment of the mapping and ablation system including cooling, ablation, anatomical navigation system, and mapping system components and a closed-loop irrigated catheter.

FIG. 2 illustrates an embodiment of the mapping and ablation system 100 including cooling, ablation, and mapping system components. The catheter 102 is configured to be introduced through the vasculature of the patient, and into one of the chambers of the heart, where it can be used to map and/or ablate myocardial tissue. The system 100 includes a radio frequency (RF) generator 202, a fluid reservoir 204 in fluid communication with a fluid pump 206, and a mapping electrode signal processor 208 coupled to the catheter 102 via the wire assembly 116 or through the connection port 114. In some embodiments, the mapping and ablation system 100 may further include an anatomical navigation system (not shown) that facilitates navigation of the catheter 102 based at least in part on signals from mapping electrode signal processor 208. The fluid reservoir 204 contains a cooling fluid that is used for cooling the distal end portion 104 of the catheter 102 during an ablation procedure. The fluid reservoir 204 and the fluid pump 206 are configured to pump the cooling fluid, such as saline, through the inner fluid lumen 108 of catheter 102 to the tip section 122.

In some embodiments, the RF generator 202 is connected to the catheter 102 through an RF wire 212. The RF generator includes an RF source 214 and a controller 216. The ablation electrode 130 is operably connected to the RF generator 202. The fluid reservoir 204 and the fluid pump 206 are connected to the catheter 102 through the connection port 114. The mapping electrode signal processor 208 is connected to the catheter 102 via a plurality of mapping electrode signal wires 218. The mapping electrode signal processor 208 is operably coupled to the one or more mapping electrodes 136 and the ring electrodes 140a-140c. Although the RF generator 202, the fluid reservoir 204 and the fluid pump 206, and the mapping electrode signal processor 208 are shown as discrete components, they can alternatively be incorporated into a single integrated device.

The RF generator 202, and in particular the RF source, is configured to generate the energy for the ablation procedure. The controller 216 controls the timing and the level of the RF energy delivered through the tip section 122. In some embodiments, the conductive material of the tip section 122 can be used to conduct RF energy generated from the RF energy generator 202 used to form lesions during the ablation procedure.

The mapping electrode signal processor 208 can be configured to detect, process, and record electrical signals within the heart via the mapping electrodes 136. Based on the detected electrical signals, the mapping electrode signal processor 208 outputs electrocardiograms (ECGs) to a display (not shown), which can be analyzed by the practitioner to determine the existence and/or location of arrhythmia substrates within the heart and/or determine the location of the catheter 102 within the heart. In an embodiment, the mapping electrode signal processor 208 generates and outputs an isochronal map of the detected electrical activity to the display for analysis by the practitioner. Based on the map, the practitioner can identify the specific target tissue sites within the heart, and ensure that the arrhythmia causing tissue has been electrically isolated by the ablative treatment.

Figure 3:
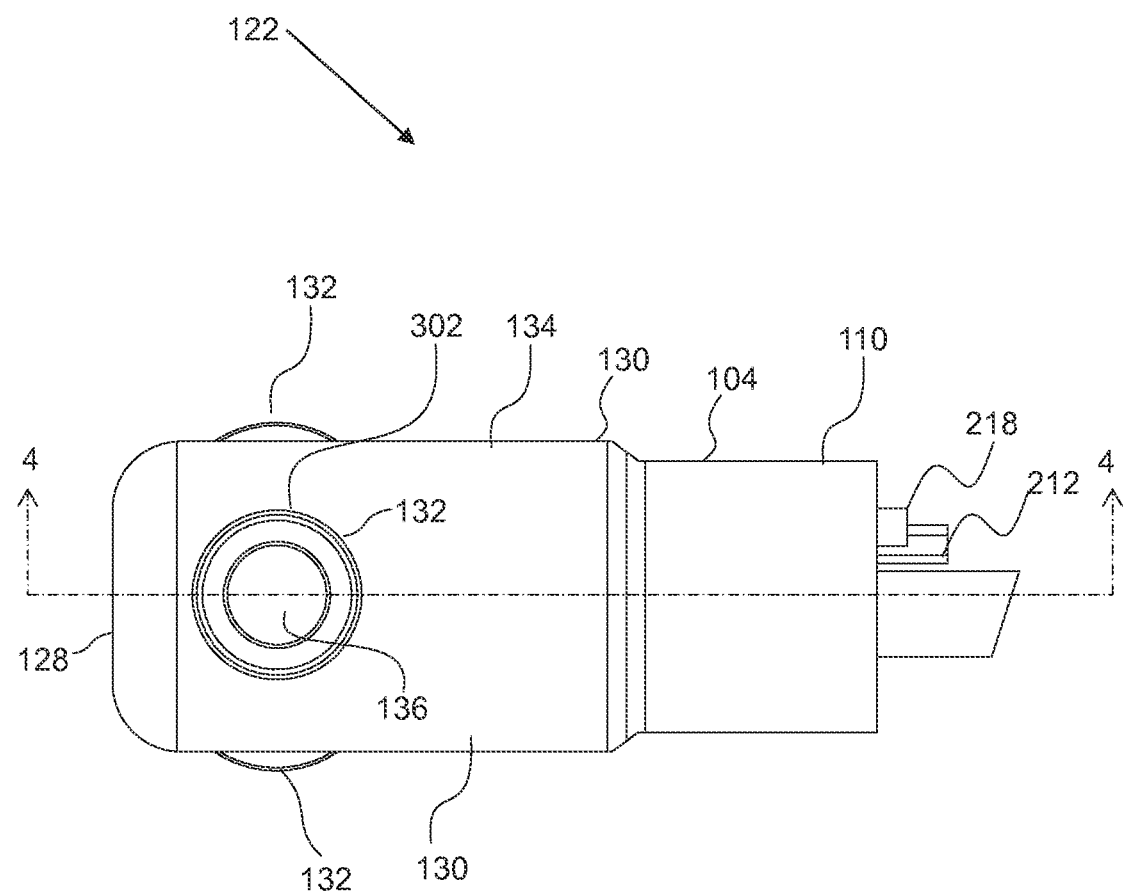
FIG. 3 is a side view of an embodiment of an ablation electrode including a plurality of mapping electrodes disposed proximate a planar distal end of a tip section.

FIG. 3 is a side view of an embodiment of the tip section 122 including an ablation electrode 130 with a planar distal end 128. In some embodiments, the tip section 122 includes a plurality of mapping electrode structures 132 exposed at the exterior surface of the ablation electrode 130. In some embodiments, each of the mapping electrode structures 132 includes a mapping electrode similar to the mapping electrode 136 and a noise artifact isolator 302.

In some embodiments, the mapping electrode structures 132 are exposed at the exterior surface 134 of the ablation electrode 130 via through holes formed in the ablation electrode 130, or are deposited on the exterior surface of the ablation electrode 130.

In some embodiments, the noise artifact isolator 302 is comprised of an electrically insulating material and can be disposed between the mapping electrode 136 and the ablation electrode 130. In some embodiments, each noise artifact isolator 302 may include multiple layers of electrical insulation to insulate each of the mapping electrodes 136 from the ablation electrode 130. In some embodiments, the noise artifact isolator 302 is embedded into the exterior surface of the ablation electrode 130. In other embodiments, the noise artifact isolator 302 is deposited on the exterior surface of the ablation electrode 130.

In some embodiments, the ablation electrode 130 is electrically coupled to the RF generator 202 (FIG. 2) so that ablation energy can be conveyed from the RF generator 202 to the ablation electrode 130 to form lesions in the target tissue. The RF wire 212 may be electrically connected to the ablation electrode 130 using suitable means such as soldering, welding, or other material bonding processes. The RF wire 212 can pass through a lumen extending through the elongate body 110 of the catheter 102, where it can be further electrically coupled to the connection port 114 (FIG. 1).

Figure 4:
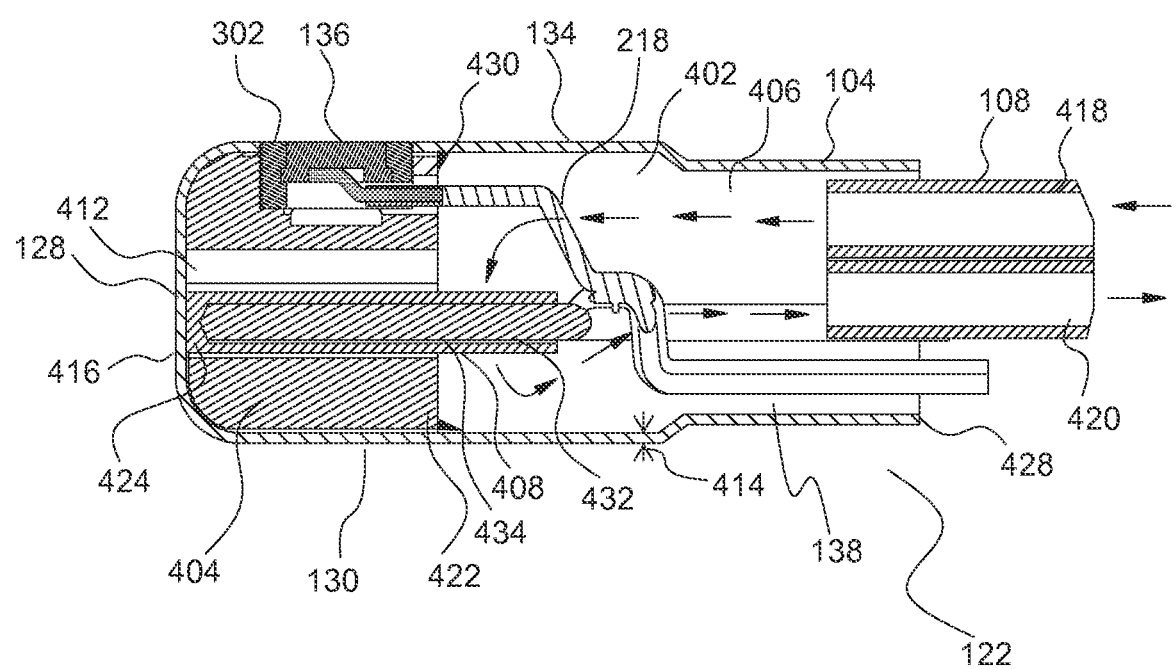
FIG. 4 is a cross-sectional view of a distal end portion of a catheter, including a planar distal end and a closed-loop irrigated catheter.
Figure 5:
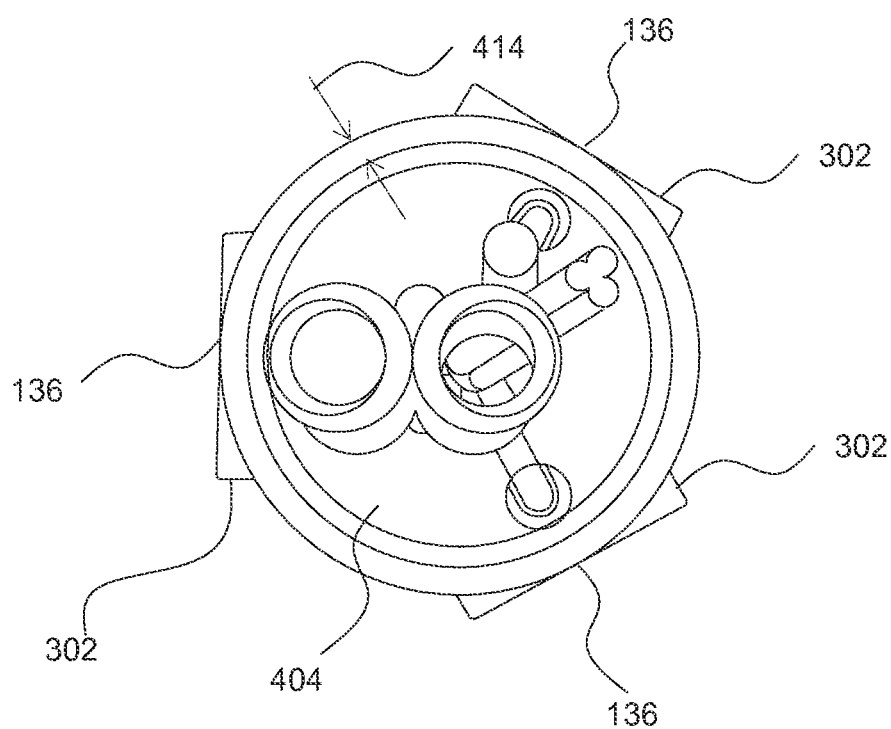
FIG. 5 is a cutaway view of an embodiment of the distal end portion of the catheter.

FIG. 4 illustrates a cross-sectional view of the tip section 122, and FIG. 5 is a cross-sectional view of the tip section 122 in a plane transverse to the view shown in FIG. 4. The distal end portion includes an open interior region 402. In some embodiments, the open interior region 402 includes the inner fluid lumen 108, a thermal mass 404, a cooling chamber 406, and a temperature sensor 408. In some embodiments, some or all of the components disposed in the open interior region 402 are arranged as an assembly that is insertable into the ablation electrode 130 during manufacturing.

The open interior region 402 is defined within the ablation electrode 130. The ablation electrode 130 along the tip section 122 has a wall thickness 414. In some embodiments, the wall thickness 414 is uniform throughout the length of the tip section 122. A uniform wall thickness provides uniform heat distribution to the target tissue from the ablation electrode 130. The substantially planar distal end 128 provides a substantially planar contact area 416 for the target tissue having a large surface area, thereby preventing localized hotspot formation at the target tissue site due to pressing of the tip section 122 into the target tissue. The substantially planar distal end 128 also allows the mapping electrodes 136 to be positioned in close proximity to the target tissue for recording localized cardiac electrical activity, thereby increasing accuracy and efficiency of the mapping electrodes 136 in recording cardiac electrical activity.

The open interior region 402 is in fluid communication with the inner fluid lumen 108. In some embodiments, the inner fluid lumen 108 includes a first inner fluid lumen 418 and a second inner fluid lumen 420. The first inner fluid lumen 418 and second inner fluid lumen 420 are in fluid communication with the fluid reservoir 204 (FIG. 2) to deliver the cooling fluid to the tip section 122 and remove the cooling fluid from the tip section.

The thermal mass 404 is disposed at the distal end portion 104 of the catheter 102. The thermal mass 404 includes a proximal portion 422 and a distal portion 424. In some embodiments, the distal portion 424 is proximal to the substantially planar distal end 128. In some embodiments, the thermal mass 404 is coupled to the ablation electrode 130 via a one or more bonding elements 430. The bonding elements 430 may be formed using any of the soldering, welding or any other material bonding process so as to mechanically and thermally couple the thermal mass 404 to the tip section 122.

The cooling chamber 406 is positioned proximally to the thermal mass 404. The cooling chamber 406 is in fluid communication with a fluid passageway 412 through the thermal mass 404. The cooling chamber 406 is also in fluid communication with the first inner fluid lumen 418 and the second inner fluid lumen 420 of the inner fluid lumen 108.

The first fluid lumen 418 is configured to deliver the cooling fluid from the fluid reservoir 204 to the cooling chamber 406. In some embodiments, the fluid reservoir 204 can push the cooling fluid from the fluid reservoir 204 into the cooling chamber 406 via the first inner fluid lumen 418. The second inner fluid lumen 420 is in fluid communication with the fluid reservoir and pump 204, and is configured to return the cooling fluid that has been circulated within the cooling chamber 406 to the fluid reservoir and pump 204. The fluid reservoir and pump 204 can extract the cooling fluid circulated within the cooling chamber 406 to the fluid reservoir 204 via the second inner fluid lumen 420. An inflow of the cooling fluid from the first inner fluid lumen 418 and an outflow of the cooling fluid from the second inner fluid lumen 420 provides a closed-loop cooling system for the ablation electrode 130.

The fluid passageway 412 is configured to allow passage of the cooling fluid through the thermal mass 404. For example, the cooling fluid can enter from the proximal portion 422 and reach the distal portion 424 of the thermal mass 404. The cooling fluid absorbs heat from the distal end 128, thereby cooling the distal end 128.

The temperature sensor 408 can be disposed into the open interior region 402 and is configured to monitor the temperature of the thermal mass 404. The temperature sensor 408 is positioned at least partially within the thermal mass 404 and comprises a material of high thermal conductivity. In some embodiments, the temperature sensor 408 extends to the distal portion 424. The thermal mass 404 includes a sensor lumen 432 extending from the proximal portion 422 to the distal portion 424. In some embodiments, the temperature sensor 408 is inserted into the thermal mass 404 through the sensor lumen 432 at the proximal portion 422. The temperature sensor 408 is coupled to a sensor wire 434. The sensor wire 434 runs along the elongate body 110 and is coupled to the wire assembly 116 at the handle 112 at the proximal end portion 106 of the catheter 102. In summary, the catheter 102 according to embodiments of the present disclosure can be used for an ablation procedure and can map intra tissue electrical activity proximal to the point of RF energy delivery. The ablation electrode 130 of the catheter 102 can be designed to have a consistent profile along the entire exterior surface 134. The ablation electrode 130 includes a substantially planar distal end 128 that ensures that the tip section 122 does not press deeper into the tissue. Additionally, the catheter 102 includes a closed-loop cooling system, wherein the cooling fluid can be circulated inside the elongate body 114, thereby preventing an infusion of the cooling fluid into the patient. The closed loop cooling system also prevents air embolisms as there is no open path for air to enter the catheter 102, and prevents entry of the cooling fluid 210 into the body of the patient.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for performing mapping and ablation functions, the system comprising:
a catheter sized and shaped for vascular access and including an elongate body extending between a proximal end and a distal end and having at least one inner fluid lumen;
a tip section positioned proximate to the distal end of the body, the tip section comprising an ablation electrode including a proximal portion and a distal portion, the distal portion having a distal end that is substantially planar, wherein the ablation electrode comprises an exterior wall that defines an open interior region within the ablation electrode;
one or more mapping electrode structures exposed at the tip section, the one or more mapping electrodes structures disposed proximate the substantially planar distal end of the ablation electrode;
a thermal mass disposed within the open interior region, the thermal mass comprising a proximal portion and a distal portion, wherein the distal portion is proximal to the substantially planar distal end of the ablation electrode;
a fluid passageway defined through the thermal mass to enable cooling fluid to pass from the proximal portion of the thermal mass to the distal portion of the thermal mass, wherein a proximal end of the fluid passageway is open and a distal end of the fluid passageway is closed by the substantially planar distal end of the ablation electrode; and
a cooling chamber in fluid communication with the at least one inner fluid lumen and the fluid passageway, and positioned proximally to the thermal mass.

2. The system of claim 1, wherein the at least one inner fluid lumen comprises:
a first inner fluid lumen extending along at least a portion of the elongate body, the first inner fluid lumen configured for fluid communication with a fluid reservoir including a cooling fluid, the first inner fluid lumen further configured to deliver the cooling fluid from the fluid reservoir to the cooling chamber; and
a second inner fluid lumen extending along at least a portion of the elongate body, the second inner fluid lumen configured for fluid communication with the fluid reservoir, the second inner fluid lumen further configured to return the cooling fluid circulated within the cooling chamber to the fluid reservoir.

3. The system of claim 1, and further comprising:
a temperature sensor positioned at least partially within the thermal mass and comprising a material of high thermal conductivity.

4. The system of claim 1, wherein the ablation electrode is configured to deliver radio frequency (RF) energy for an RF ablation procedure.

5. The system of claim 4, wherein the one or more mapping electrode structures are formed on the ablation electrode.

6. The system of claim 5, wherein the one or more electrode structures each comprise a mapping electrode and a noise artifact isolator comprising an electrical insulator disposed between the mapping electrode and the ablation electrode.

7. The system of claim 1, wherein the one or more mapping electrode structures are disposed within about 1.0 mm of the planar distal end of the tip section.

8. The system of claim 1, and further comprising one or more mapping ring electrodes disposed on the body proximal to the one or more electrode structures.

9. A system for performing mapping and ablation functions, the catheter system comprising:
a radio frequency (RF) generator;
a fluid reservoir and a pump;
a mapping signal processor;
a catheter sized and shaped for vascular access and including an elongate body extending between a proximal end and a distal end and having at least one inner fluid lumen coupled to the pump, wherein the pump is configured to pump fluid from the fluid reservoir into the at least one inner fluid lumen;
an ablation electrode coupled to the distal end of the body, and operably connected to the RF generator, the ablation electrode including an exterior wall that defines an open interior region within the ablation electrode, the ablation electrode including a proximal portion and a distal portion, the distal portion having a distal end that is substantially planar;
one or more mapping electrodes structures operably connected to the mapping signal processor, the one or more mapping electrode structures exposed at an exterior of the ablation electrode proximate the substantially planar distal end;
a thermal mass disposed within the open interior region, the thermal mass comprising a proximal portion and a distal portion, wherein the distal portion is proximal to the substantially planar distal end of the ablation electrode;
a fluid passageway defined through the thermal mass to enable cooling fluid to pass from the proximal portion of the thermal mass to the distal portion of the thermal mass, wherein a proximal end of the fluid passageway is open and a distal end of the fluid passageway is closed by the substantially planar distal end of the ablation electrode; and
a cooling chamber in fluid communication with the at least one inner fluid lumen and the fluid passageway, and positioned proximally to the thermal mass.

10. The system of claim 9, wherein the one or more electrode structures each comprise a mapping electrode and a noise artifact isolator comprising an electrical insulator disposed between the mapping electrode and the ablation electrode.

11. The system of claim 9, wherein the at least one inner fluid lumen comprises:
a first inner fluid lumen extending along at least a portion of the elongate body, the first inner fluid lumen in fluid communication with the fluid reservoir and pump such that the pump pushes cooling fluid from the fluid reservoir to the cooling chamber via the first inner fluid lumen; and
a second inner fluid lumen extending along at least a portion of the elongate body, the second inner fluid lumen in fluid communication with the fluid reservoir and pump such that the pump pulls the cooling fluid circulated within the cooling chamber to the fluid reservoir via the second inner fluid lumen.

12. A system for performing mapping and ablation functions, the system comprising:
a catheter sized and shaped for vascular access and including an elongate body extending between a proximal end and a distal end and having at least one inner fluid lumen;
an ablation electrode coupled to the distal end of the catheter body, the ablation electrode configured to deliver radio frequency (RF) energy for an RF ablation procedure, the ablation electrode including an exterior wall that defines an open interior region within the ablation electrode, the ablation electrode including a proximal portion and a distal portion, wherein the distal portion has a distal end that is substantially planar;

a thermal mass within the open interior region, the thermal mass comprising a proximal portion and a distal portion wherein the distal portion is proximal to the substantially planar distal end of the ablation electrode;

a fluid passageway defined through the thermal mass to enable cooling fluid to pass from the proximal portion of the thermal mass to the distal portion of the thermal mass, wherein a proximal end of the fluid passageway is open and a distal end of the fluid passageway is closed by the substantially planar distal end of the ablation electrode;

a cooling chamber in fluid communication with the at least one inner fluid lumen of the elongate body and the fluid passageway, and positioned proximally to the thermal mass; and one or more mapping electrode structures exposed at an exterior of the ablation electrode.

13. The system of claim 12, and further comprising one or more mapping ring electrodes disposed on the body proximal to the one or more electrode structures.

14. The system of claim 12, wherein the one or more electrode structures each comprise a mapping electrode and a noise artifact isolator comprising an electrical insulator disposed between the mapping electrode and the ablation electrode.

15. The system of claim 12, wherein the at least one inner fluid lumen comprises:

a first inner fluid lumen extending along at least a portion of the elongate body, the first inner fluid lumen configured for fluid communication with a fluid reservoir including a cooling fluid, the first inner fluid lumen further configured to deliver the cooling fluid from the fluid reservoir to the cooling chamber; and a second inner fluid lumen extending along at least a portion of the elongate body, the second inner fluid lumen configured for fluid communication with the fluid reservoir, the second inner fluid lumen further configured to return the cooling fluid circulated within the cooling chamber to the fluid reservoir.

16. The system of claim 12, and further comprising one or more mapping ring electrodes disposed on the body proximal to the one or more electrode structures, the one or more ring electrodes operably connected to a mapping signal processor.

* * * * *